(12) United States Patent
Kumar et al.

(10) Patent No.: US 7,462,712 B2
(45) Date of Patent: Dec. 9, 2008

(54) PROCESS FOR THE PREPARATION OF IMIPENEM

(75) Inventors: Yatendra Kumar, Haryana (IN); Neera Tewari, Haryana (IN); Bishwa Prakash Rai, Uttar Pradesh (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 267 days.

(21) Appl. No.: 10/477,776

(22) PCT Filed: May 15, 2002

(86) PCT No.: PCT/IB02/01670

§ 371 (c)(1),
(2), (4) Date: Jun. 16, 2004

(87) PCT Pub. No.: WO02/094828

PCT Pub. Date: Nov. 28, 2002

(65) Prior Publication Data

US 2004/0220168 A1    Nov. 4, 2004

(30) Foreign Application Priority Data

May 18, 2001  (IN) .............................. 594/DEL/01

(51) Int. Cl.
*C07D 477/20* (2006.01)
(52) U.S. Cl. .................................. 540/350
(58) Field of Classification Search ................ None
See application file for complete search history.

(56) References Cited

U.S. PATENT DOCUMENTS

| 4,194,047 A | | 3/1980 | Christensen et al. ........ 546/272 |
| 4,292,436 A | | 9/1981 | Liu et al. ................... 560/148 |
| 4,374,772 A | | 2/1983 | Hazen et al. .............. 260/245.2 |
| 4,640,915 A | * | 2/1987 | Hashimoto et al. ...... 514/210.11 |
| 4,644,061 A | * | 2/1987 | Kim ........................... 540/350 |
| 4,745,188 A | * | 5/1988 | Christensen et al. ........ 540/350 |
| 4,782,051 A | * | 11/1988 | Christensen et al. ... 514/210.09 |
| 4,894,450 A | | 1/1990 | Grabowski et al. .......... 540/350 |
| 5,245,069 A | * | 9/1993 | McManus ................... 558/148 |
| 5,608,056 A | * | 3/1997 | Murata et al. ............... 540/350 |
| 5,672,701 A | * | 9/1997 | Martel et al. ................ 540/350 |
| 7,241,885 B2 | * | 7/2007 | Kumar et al. ............... 540/350 |
| 2004/0054167 A1 | * | 3/2004 | Kumar et al. ............... 540/350 |
| 2004/0220168 A1 | * | 11/2004 | Kumar et al. ............ 514/210.1 |
| 2006/0167243 A1 | * | 7/2006 | Bae et al. .................... 540/350 |

FOREIGN PATENT DOCUMENTS

WO    WO 02/36594    5/2002

OTHER PUBLICATIONS

Scriven, Chem. Soc. Rev., 1983, 12, 129-161.*
Lianan et al., Hua Gong Jin Zhan Kai Fu Ying Yong vol. 6, 1998, pp. 43-45 (with translation).*
Hofle, Angew. Chem. Int. Ed. 17, 569 (1978).*

* cited by examiner

*Primary Examiner*—Mark L Berch
(74) *Attorney, Agent, or Firm*—Jayadeep R. Deshmukh, Esq.; George E. Heibel, Esq.

(57) ABSTRACT

The present invention relates to an improved process for the preparation of imipenem comprising reacting a bicyclo ketone precursor of the Formula II,

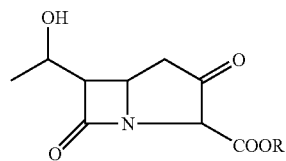

FORMULA II wherein R is a protecting group, with a phosphorohalidate in the presence of a base and a catalytic amount of dialkylaminopyridine.

12 Claims, No Drawings

PROCESS FOR THE PREPARATION OF IMIPENEM

FIELD OF THE INVENTION

The present invention relates to an improved, cost effective and industrially advantageous process for the preparation of imipenem.

BACKGROUND OF THE INVENTION

Imipenem monohydrate of Formula I which is the N-formimidoyl derivative of thienamycin and has the structural Formula I.

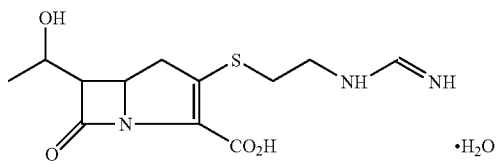

FORMULA I

It is the first clinically available member of a new class of β-lactam antibiotics that possess the carbapenem ring system. Imipenem exhibits an extremely broad spectrum of activity against gram-positive and gram-negative aerobic and anaerobic species, which is partly due to its high stability in the presence of β-lactamases.

Imipenem was first disclosed in U.S. Pat. No. 4,194,047. Several general methods for the preparation of N-methylene derivatives of thienamycin including imipenem have been outlined in U.S. Pat. No. 4,194,047 starting from thienamycin. The process for the preparation of imipenem has been found to give the product in low yield and of poor quality due to inherent instability of the starting compound i.e. thienamycin.

U.S. Pat. No. 4,292,436 provides an alternate method for the preparation of imipenem from bicyclo ketone precursor of Formula II,

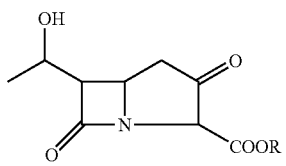

FORMULA II wherein R is a protecting group, comprising activating the keto ester and reacting the activated keto ester with N-formimidoyl-2-aminoethanethiol to obtain carboxyl protected imipenem which gives imipenem after hydrogenation. However, the process gives low yields of the final product (59% in solution and 35% of isolated imipenem monohydrate).

U.S. Pat. No. 4,374,772 gives an improved process for preparing imipenem from dilute aqueous solutions of thienamycin using benzylic formimidate reagents. However, the process has the disadvantage of producing at least 5% of dimmer bis-thienamycin formamidene along with the desired proudct imipenem.

U.S. Pat. No. 4,894,450 uses new reagents—bis (chloro-substituted phenyl) phosphorochloridate to activate the bicycloketone precursor of formula II, wherein R is a protecting group. Subsequent reaction with cysteamine hydrochloride, amidine formation and hydrogenolysis of the ester group gives good yield of imipenem. However, the reagent employed for activation is not available commercially and its preparation involves a cumbersome multistage purification process.

In light of the above drawbacks in the prior art processes, there is a need for the development of a process for the preparation of imipenem which is convenient to operate on an industrial scale, employs readily and commercially available raw materials and reagents and which process gives substantially pure product in good yield.

SUMMARY OF THE INVENTION

It is an object of the present invention to solve the problems associated with the prior art and provide an efficient process. The process provides obvious benefits with respect to economics and convenience to operate on a commercial scale.

Accordingly, the present invention relates to an improved process for the preparation of imipenem of sufficient purity and high yield starting from the bicyclo ketone precursor of formula II, wherein R is a protecting group.

In particular, the present invention relates to a process for the preparation of imipenem of Formula I

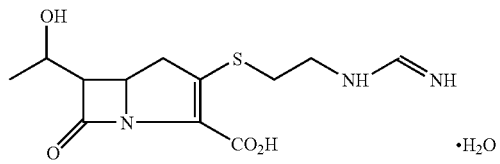

FORMULA I comprising:
  a) activating a keto ester compound of Formula II,

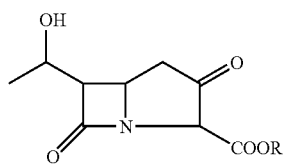

FORMULA II wherein R is a protecting group, with a phosphorohalidate of Formula VI,

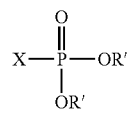

FORMULA VI wherein X is a halogen atom and R' is aryl, in the presence of a base and a catalytic amount of a dialkylaminopyridine, to obtain enol phosphate compound of Formula III,

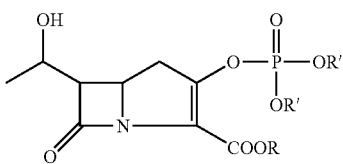

FORMULA III wherein R and R' have the same meaning as defined above, b) reacting the enol phosphate intermediate of Formula III, in situ with 2-aminoethanethiol or an acid addition salt thereof to get thienamycin ester of Formula IV,

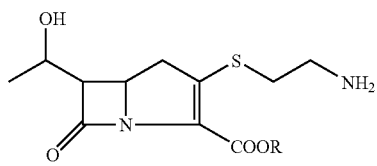

FORMULA IV wherein R has the same meaning as defined above, c) reacting thienamycin ester of Formula IV in situ with benzyl formimidate or an acid addition salt thereof in the presence of a base to get carboxyl protected imipenem of Formula V,

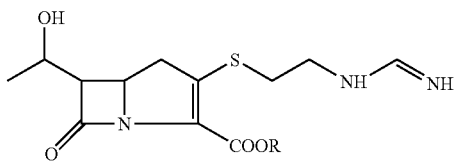

FORMULA V wherein R has the same meaning as defined above, and d) hydrogenating the carboxyl protected imipenem of formula V in an aqueous medium to obtain imipenem.

The reactions at steps a) and c) are preformed in the presence of a base which may be a secondary amine or a tertiary amine. Examples of secondary amines include diisopropylamine, dicyclohexylamine, 2,2,6,6-tetramethylethylpiperidine (TMP) and 1,1,3,3-tetramethylguanidine (TMG). Examples of suitable tertiary amines include diisopropylethylamine, triethylamine and tributylamine.

The presence of a catalytic amount of dialkylaminopyridine at step a) prevents the formation of impurity of formula VII,

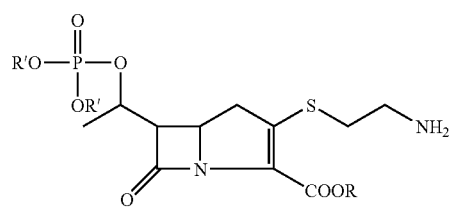

FORMULA VII

The impurity of Formula VII is formed in substantial quantities (14-15% by HPLC) by side reaction of the hydroxymethyl group at the 6-position of the carbapenem.

Dialkylaminopyridines are used in catalytic amounts, preferably in the range of about 0.5 to 2% w/w relative to the keto ester of Formula II. For the purpose of the present invention, dialkylaminopyridine includes pyridine substituted at the 2- or 4-position. Examples of such dialkylamino substituents include N,N-dimethylamino, N,N-diethylamino, N,N-dicyclohexylamino, N-cyclohexyl-N-methylamino, 1-pyrrolidinyl, 1-piperidinyl and mixture(s) thereof.

The protecting group R in the compound of Formula II is any carboxylic acid protecting group which may be easily removed by hydrogenation, such as benzyl, p-nitrobenzyl or methoxymethyl.

In the compound of Formula VI, X is a halogen atom which may be chloro, bromo or iodo. Particularly preferred is chloro. R' in the compound of Formula VI is aryl, preferably phenyl, which may be substituted.

Compounds of Formula II, VI and benzylformimidate or its acid addition salts may be obtained by methods known in the art.

The reaction at step a) is carried out in an organic solvent such as N,N-dimethylacetamide (DMAc), N,N-dimethylformamide (DMF), N-methylpyrrolidone (NMP), ethylacetate, dichloromethane, tetrahydrofuran, or mixture(s) thereof. Preferably a mixture of dichloromethane and any of the solvents chosen from DMAc, DMF or NMP is used. The reaction at step b) is carried out at a temperature of from about −50 to −75° C., preferably at about −60 to −75° C.

Steps a), b) and c) are performed in situ, thus the solvent and the base are common to the three steps. Additional amount of the base is added to facilitate the reaction at step c).

Acid addition salts of 2-aminoethanethiol and benzylformimidate used at steps b) and c) respectively may be the same or different and may arise from either organic or inorganic acids. Examples of such salts include hydrochloride, hydrobromide, hydroiodide, sulfate, methanesulfonate, benzenesulfonate, fumarate, tartrate, thiocyanate, tosylate, phosphate, picrate, succinate, pivalate, benzoate, acetate and citrate salts. Particularly preferred are the hydrochloride salts of both 2-aminoethanethiol and benzylformimidate.

The hydrogenation step d) is carried out after suitable aqueous work up of the reaction mixture from step c). Preferably, a lower alcohol is added to the obtained aqueous solution of compound V and hydrogenation carried out at a pH of about 7 to 8 in the presence of N-methylmorpholine buffer. Examples of lower alcohols which may be added include methanol, ethanol, isopropanol and propanol. The hydrogenation may be carried out using any of the metal cataylsts such as platinum oxide, platinum/carbon, palladium hydroxide and palladium/carbon.

Imipenem is obtained as a solution after hydrogenation and filtration of the catalyst. Imipenem may then be isolated from the solution in the usual manner by lyophilization and/or crystallization methods known in the art but is preferably crystallized by the method described in the patent application filed concurrently herewith.

DETAILED DESCRIPTION OF THE INVENTION

In the following section one preferred embodiment is described by way of example to illustrate the process of the invention. However, it is not intended in any way to limit the scope of the present invention.

PREPARATION OF IMIPENEM

EXAMPLE 1

Step a)—Preparation of Enol Phosphate Intermediate

A solution of p-nitrobenzyl (3R, 5R, 6S)-2oxo-6-[(1R)-1-hydroxyethyl)] carbapenem-3-carboxylate (30 g) was dissolved in a mixture of N, N-dimethylacetamide (300 ml) and dichloromethane (150 ml). The solution was cooled to −55° C. and 4-(dimethylamino)pyridine (0.17 g) was added followed by diisopropylethylamine (26.7 g). The mixture was stirred for 5 min. at −55° C. and then a solution of diphenylchlorophosphate (25.4 g) in dichloromethane (30 ml) was added dropwise at −55 to −45° C. The reaction mixture thus obtained was stirred further for 30 minutes to obtain the enol phosphate ester.

Step b)—Preparation of Thienamycin Ester

The reaction mixture from step a) was further cooled to −70 to −75° C. and a solution of 2-aminoethanethiol hydrochloride (12 g) in N,N-dimethylacetamide (60 ml) was added in 10 min at −75 to −60° C. The reaction mixture was stirred for another 60 min. to produce p-nitrobenzyl ester of thienamycin.

Step c)—Preparation of p-Nitrobenzyl Ester of Imipenem

To the above reaction mixture from step b), was added diisopropylethylamine (16.0 g) and benzyl formimidate hydrochloride (20.0 g) at −50 to −55° C. The reaction mixture was maintained for about one and a half hour at the same temperature. The temperature was then raised to −20° C. in 20-30 min and the reaction mixture stirred for 20-30 min at this temperature to obtain the imipenem ester.

Step d)—Preparation of Imipenem

The above clear solution of step c) was poured into a mixture of water (300 ml), isopropanol (150 ml) and N-methylmorpholine (26 g) maintained at 5-10° C. and the pH of the solution adjusted to 7.0 to 7.5. The solution was hydrogenated at 3-4 kg pressure for 2.5 hour at 10-25° C. over palladium/carbon. The mixture was filtered and assayed for imipenem (80%, as determined by HPLC).

While the present invention has been described in terms of its specific embodiments, certain modifications and equivalents will be apparent to those skilled in the art and are intended to be included within the scope of the present invention.

We claim:

1. A process for the preparation of imipenem of Formula I

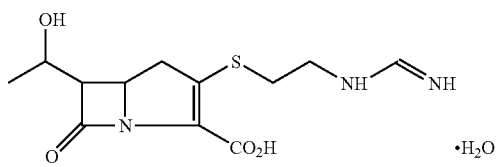

FORMULA I the process comprising:

a) activating a keto ester compound of Formula II,

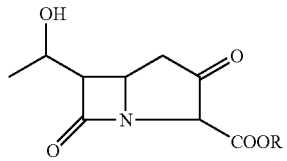

FORMULA II wherein R is a protecting group with a phosphorohalidate of Formula VI

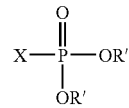

FORMULA VI wherein X is a halogen atom and R' is phenyl, in the presence of a base and a catalytic amount of a dialkylaminopyridine to obtain enol phosphate compound of Formula III,

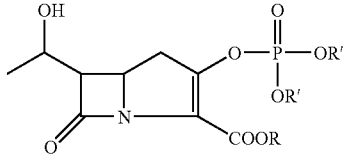

FORMULA III wherein R and R' have the same meaning as defined above, b) reacting the enol phosphate intermediate of Formula III, in situ with 2-aminoethanethiol or an acid addition salt thereof to get thienamycin ester of Formula IV,

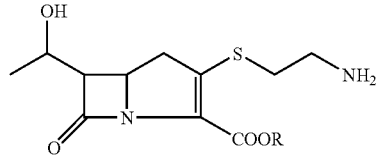

FORMULA IV wherein R has the same meaning as defined above, c) reacting thienamycin ester of Formula IV in situ with benzyl formimidate or an acid addition salt thereof in the presence of a base to get carboxyl protected imipenem of Formula V,

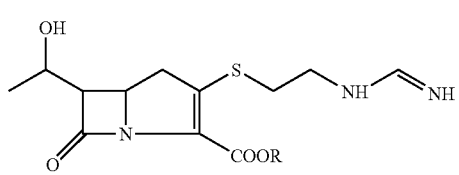

FORMULA V wherein R has the same meaning as defined above, and d) hydrogenating the carboxyl protected imipenem of formula V obtained from step c), without isolation or purification, in an aqueous medium to obtain imipenem.

2. The process of claim 1 wherein the dialkylaminopyridine is 4-(dimethylamino)pyridine.

3. The process of claim 1 wherein the base used at step a) and step c) is a secondary amine or a tertiary amine.

4. The process of claim 3 wherein said base is selected from the group consisting of diisopropylamine, dicyclohexylamine, 2,2,6,6-tetramethyl ethylpiperidine (TMP), 1,1,3,3-tetramethylguanidine(TMG), diisopropylethylamine, triethylamine, tributylamine, and mixture(s) thereof.

5. The process of claim 1 wherein the protecting group R is benzyl, p-nitrobenzyl or methoxymethyl in the compound of Formula II.

6. The process of claim 1 wherein the reaction at step a) is performed in an organic solvent.

7. The process of claim 6 wherein said organic solvent is selected from the group consisting of N,N-dimethylacetamide, N,N-dimethylformamide, N-methylpyrrolidone, ethyl acetate, dichloromethane, tetrahydrofuran, and mixture(s) thereof.

8. The process of claim 6 wherein the reaction at step a) is performed in a mixture of dichloromethane and one of the solvents selected from N,N-dimethylacetamide, N, N-dimethyl formamide and N-methylpyrrolidone.

9. The process of claim 1 wherein the reaction at step b) is performed at a temperature of from about −60 to −75° C.

10. The process of claim 1 wherein R' is phenyl in the compound of Formula III.

11. The process of claim 1 wherein the hydrogenation at step d) is carried out in an aqueous medium comprising a mixture of water and a lower alcohol.

12. The process of claim 11 wherein the lower alcohol is selected from the group consisting of methanol, ethanol, isopropanol, and propanol.

* * * * *